(12) United States Patent
Allen et al.

(10) Patent No.: US 7,067,291 B2
(45) Date of Patent: Jun. 27, 2006

(54) BIOCATALYTIC PREPARATION OF ENANTIOMERICALLY ENRICHED AMINOPENTANENITRILE

(75) Inventors: David R. Allen, LaGrange Park, IL (US); Vadim V. Mozhaev, Hoffman Estates, IL (US); Rao H. Valivety, Schaumburg, IL (US)

(73) Assignee: Pfizer Inc., New York, NY (US)

( * ) Notice: Subject to any disclaimer, the term of this patent is extended or adjusted under 35 U.S.C. 154(b) by 323 days.

(21) Appl. No.: 10/327,492

(22) Filed: Dec. 20, 2002

(65) Prior Publication Data

US 2004/0121435 A1    Jun. 24, 2004

(51) Int. Cl.
C12P 13/00 (2006.01)
(52) U.S. Cl. ...................... 435/128; 435/280
(58) Field of Classification Search ................. 435/128, 435/129, 280
See application file for complete search history.

(56) References Cited

U.S. PATENT DOCUMENTS

| | | | |
|---|---|---|---|
| 4,950,606 | A | 8/1990 | Stirling et al. |
| 5,300,437 | A | 4/1994 | Stirling et al. |
| 5,728,876 | A | 3/1998 | Balkenhohl et al. |
| 5,981,267 | A | 11/1999 | Wong et al. |
| 6,214,608 | B1 | 4/2001 | Balkenhohl et al. |

FOREIGN PATENT DOCUMENTS

| | | |
|---|---|---|
| EP | 0859060 A2 | 8/1998 |
| EP | 1013773 A1 | 6/2000 |
| EP | 1087018 A1 | 3/2001 |
| WO | WO 91/19002 A1 | 12/1991 |
| WO | WO 98/50575 A1 | 12/1998 |
| WO | WO 99/31264 A1 | 6/1999 |
| WO | WO 02/20820 A1 | 3/2002 |
| WO | WO 02/20821 A2 | 3/2002 |

OTHER PUBLICATIONS

Svedas et al., "Enantioselective Penicillin Acylase-catalyzed Reactions", Annals New York Academy of Sciences, pp. 659-669.
Rosell et al., "Resolution of Racemic Mixtures through Stereospecific Kintetically Controlled Synthesis Catalyzed by Penicillin G Acylase Derivatives", Annals New York Academy of Sciences, pp. 425-428.
Reeve et al., "Biocatalysis-A flexible tool for the prepararation of optically active amines and amides", Chimica OGGI/chemistry today, pp. 31-34 (Jul./Aug. 2001).
Arroyo et al., "Prediction of penicillin V acylase stability in water-organic co-solvent monophasic systems as a function of solvent composition", Enzyme and Microbial Technology 27, pp. 122-126 (2000).
Cardillo et al., "Enzymatic Resolution of a-Alkyl B-Amino Acids Using Immobilized Penicillin G Acylase", J. Org. Chem. vol. 61, No. 24, pp. 8651-8654 (1996).
Chadha et al., "Penicillin Amidase: Chemospecificity and Stereospecificity", Int' Journal of Pharm Advances, vol. 1, No. 2, pp. 216-229 (Oct. 1995).
Hacking et al., "Lipase and Esterase-Catalyzed Acylation of Hetero-Substituted Nitrogen Nucleophiles in Water and Organic Solvents", Biotechnology and Bioengineering, vol. 68, No. 1, pp. 84-91 (Apr., 2000).
Heby et al., "Stereoselective transformation of amines to alcohols enriched with the enantiomer formed by respectively inversion and retention of configuration", Tetrahedron: Asymmetry, vol. 8, No. 13. pp. 2193-2198 (1997).
Brieva et al., "Enzymatic Synthesis of Amides with Two Chiral Centres", J. Chem. Soc., Chem. Commun. pp. 1386-1387 (1990).
Davis et al., "Resolution of Chiral Alphatic and Arylalkyl Amines Using Immobilized Candida Antartica Lipase and Isolation of Their R- and S-Wnantiomers", Synthetic Communications vol. 31, No. 4, pp. 569-578 (2001).
Fernandez et al., "Lipase-catalysed Enantioselective Acylation of N-Protected or Unprotected 2-Aminoalkan-1-ols", J. Chem. Soc. pp. 2885-2889 (1992).
Garcia et al., "Lipase-Catalyzed Aminolysis and Ammonolysis of B-ketoesters. Synthesis of Optically Active B-ketoamides." Tetrahedron vol. 50. No. 23, pp. 6935-6940 (1994).
Garcia-Urdiales et al., "Enzymatic one-pot resolution of two nucleophiles: alcohol and amine", Tetrahedron: Assymnetry vol. 11, pp. 1459-1463 (2000).
Gotor et al., "Synthesis of Optically Active Amides from B-Furyl and B-Phenyl Esters by way of Enzymatic Aminolysis", J. Chem. Soc. , pp. 2453-2456 (1993).
Iglesias et al., "Candida antarctica B lipase catalysed resolution of (+) -1-(heteroraryl)etylamines", Tetrahedron: Asymmetry, vol. 8, No. 16, pp. 2675-2677 (1977).
Maestro et al., "Enzymatic resolution of (+)-trans-2-aminocyclohexanol and (+) -trans-2-aminocyclopentanol", Tetrahedron: Asymmetry, vol. 8, No. 18, pp. 3153-3159 (1977).
Maugard et al., "Lipase-Catalyzed Chemoselective N-Acylation of Amino-Sugar Derivatives in Hydrophobic Solvent: Acid-Amine Ion-Pair Effects", Tetrahedron vol. 53, No. 22, pp. 7587-7594 (1997).

(Continued)

Primary Examiner—Herbert J. Lilling
(74) Attorney, Agent, or Firm—Gregg C. Benson; Lisa A. Samuels

(57) ABSTRACT

Methods for preparing enantiomerically enriched aminopentanenitriles are provided. The methods involve selective acylation of an enantiomeric mixture of 3-aminopentanenitrile or selective hydrolysis of an enantiomeric mixture of 3-aminopentanenitrile amide in the presence of an enzyme selected from the group comprising lipase, esterase, and acylase. The methods yield R-aminopentanenitrile, which can be used to produce pharmaceutical products.

4 Claims, No Drawings

OTHER PUBLICATIONS

Messina et al., "Resolution of (+)-1-Aryl-2-propynylamines via Acyltransfer Catalyzed by *Candida antarctica* Lipase", J. Org. Chem. vol. 64, pp. 3767-3769 (1999).

Morgan et al., "Enzymatic Kinetic Resolution of Piperidine Atropisomers: Synthesis of a Key Intermediate of the Farnesyl Protein Trasferase Inhibitor, SCH66336", J. Org. Chem. vol. 65, No. 18, pp. 5451-5459 (2000).

Ohrner et al,. "Kinetic resolutions of amine and thiol analogues of secondary alcohols catalyzed by the *Candid antarctica* lipase B", Enzyme and Microbial Technology vol. 19, pp. 328-331 (1996).

Orsat et al., "Homocarbonates as Substrates for the enantioselective Enzymatic Protection of Amines", J. Am. Chem. Soc. vol. 118, pp. 712-713 (1996).

Orsini et al., "Study of the resolution of amino acids and aminoalcohols in organic solvents", Amino Acids vol. 9, pp. 135-140 (1995).

Pozo et al., "Chiral Carbamates through an Enzymatic Alkoxycarbonylation Reaction", Tetrahedron vol. 49, No. 20, pp. 4321-4326 (1993).

Takayama et al., "Designing enzymatic resolution of amines", Chem. Communi., pp. 127-128 (1999).

Kitaguchi et al., "Enzymatic Resolution of Racemic Amines: Crucial Role of the Solvent", J. Am. Chem. Soc. vol. 111, pp. 3094-3095 (1989).

Takayama et al., "Enzymatic Resolution of Amines and Amino Alcohols Using Pent-4-enoyl Derivative", Tetrahedron Letters, vol. 37, No. 35, pp. 6287-6290 (1996).

Seledad de Castro et al., "Lipase-Catalyzed Synthesis of Chiral Amides. A Systematic Study of the Variables that Control the Synthesis", Tetrahedron vol. 54, pp. 2877-2892 (1998).

Guranda et al., "Highly efficient and enantioselective enzymatic acylation of amines in aqueous medium". Tetrhedron: Asymmetry vol. 12, pp. 1645-1650 (2001).

Quiros et al., "Lipase-Catalyzed Synthesis of Optically Active Amides in Organic Media", Tetrahedron: Asymmetry vol. 4, No. 6, pp. 1105-1112 (1993).

Langen et al., "Penicillin acylase-catalyzed resolution of amines in aqueous organic solvents", Tetrahedron: Asymmetry vol. 11, pp. 4593-4600 (2000).

Topgi et al., "Use of Enzyme Penicillin Acylase in Selective Amidation/Amide Hydrolysis to Resolve Ethyl 3-amino-4pentynoate Isomers", Bioorganic & Medicinal Chemistry vol. 7, pp. 2221-2229 (1999).

Landis et al., "Kinetic Resolution of B-Amino Esters by Acylation Using Immobilized Penicillin Amidohydrolase", Organic Process Research & Development vol. 6, pp. 539-546 (2002).

Youshko et al., "Enantioselective acylation of chiral amines catalysed by aminoacylase I", Tetrahedron: Asymmetry vol 12, pp. 3267-3271 (2001).

Fadnavis et al. "Resolution of racemic 2-amino-1-butanol with immobilised penicillin G acylase", Tetrahedron: Asymmetry vol. 10, pp. 4495-4500 (1999).

Boller et al., Untitled, Organic Press Research & Developemnt vol. 6, pp. 509-519 (2002).

Balkenhohol et al., "Optically active Amines via Lipase-Catalyzed Methoxyacetylation", J. prakt. Chem. vol. 339, pp. 381-384 (1997).

Lopez-Serrano et al., "Enantioselective acylation of a-aminonitriles catalysed by *Candida antarctica* lipase. An unexpected turnover-related racemisation.", Tetrahedron: Asymmetry vol. 12, pp. 219-228 (2001).

BIOCATALYTIC PREPARATION OF ENANTIOMERICALLY ENRICHED AMINOPENTANENITRILE

FIELD OF INVENTION

The present invention relates to the biocatalytic resolution of chiral aminopentanenitrile compounds.

BACKGROUND OF THE INVENTION

Chiral resolution of racemic amines is a very important process for the pharmaceutical industry, as these amines are useful intermediates for the production of various antibiotics or as inhibitory transmitters to control some neurological disorders. The biological activities are strongly dependent on their absolute configuration and both S and R isomers have potential therapeutic uses. Traditionally, chemical chiral resolution is achieved by utilizing a chiral compound such as an acid to stereo-selectively react with one of the isomers, and thereby facilitating the separation of the enantiomers.

3-Aminopentanenitrile (APN) is a commercially available compound, which may exist in two enantiomeric forms, R-APN and S-APN. Typically, chiral resolution of R-APN is achieved by reacting a racemic mixture of APN with dibenzoyl-L-tartaric acid, which preferentially binds to R-APN. The resulting R-APN-dibenzoyl-L-tartrate salt may be isolated and subsequently reacted with methanesulfonic acid to produce R-APN-methanesulfonate salt.

Efficient, economic and convenient alternative methods for the chiral resolution of aminopentanenitriles are needed. Biocatalytic processes can furnish the requisites, as enzymes often exhibit excellent enantioselectivities. Further, enzyme reactions are well characterized for their specificities and mild reaction conditions. The application of enzymes for the chiral resolution of APN has not been disclosed.

SUMMARY OF THE INVENTION

Methods for preparing enantiomerically enriched aminopentanenitriles are provided. The methods involve a selective acylation reaction, in which an enantiomeric mixture of 3-aminopentanenitrile (APN) is reacted with an acyl donor in the presence of a biocatalyst. The reaction results in a mixture of an acylated enantiomer and a non-acylated enantiomer. The acylated enantiomer may be R-APN amide or S-APN amide, depending on the selectivity of the biocatalyst. The acylated enantiomer may be separated from the non-acylated enantiomer, and subsequently hydrolyzed to produce the other non-acylated enantiomer.

Alternatively, the methods may involve selective hydrolysis of an enantiomeric mixture of acylated APN, in the presence of a biocatalyst. The selective hydrolysis yields a mixture of an acylated enantiomer and a non-acylated enantiomer. The acylated enantiomer may be separated from the non-acylated enantiomer, and then hydrolyzed to produce the other non-acylated enantiomer.

In addition, the methods may be based on a chemical or enzymatic acylation of an enantiomeric mixture of APN to produce an enantiomeric mixture of acylated APN, which is used as a substrate for selective hydrolysis as described above.

Specifically, in one embodiment of the present invention, a method for preparing enantiomerically enriched APN comprises the steps of providing an enantiomeric mixture containing R-APN and S-APN, and reacting the enantiomeric mixture with an acyl donor in the presence of an enzyme to selectively acylate either one of the enantiomers to produce either a mixture of S-APN and acylated R-APN, or a mixture of R-APN and acylated S-APN. The method may further include the step of separating the acylated and non-acylated enantiomers to produce enantiomerically enriched acylated R-APN or non-acylated R-APN. A further step may involve hydrolyzing acylated R-APN to produce R-APN. Suitable enzymes that show enantioselectivity for acylation of APN include lipases and esterases. A further step may include reacting R-APN with dibenzoyl-L-tartaric acid to produce R-APN-dibenzoyl-L-tartrate which may be further reacted with methanesulfonic acid to form methanesulfonate salt.

In another embodiment, the method for preparing enantiomerically enriched APN includes the steps of providing an enantiomeric mixture containing acylated R-APN and acylated S-APN, and selectively hydrolyzing either acylated R-APN or acylated S-APN in the presence of a biocatalyst. Specifically, penicillin acylase is a suitable enzyme, which has enantioselectivity for hydrolysis of acylated S-APN. In a specific reaction using penicillin acylase, a mixture of R-APN-amide and S-APN is produced.

The method may further include the steps of separating R-APN-amide from S-APN, recovering R-APN-amide, and non-selectively hydrolyzing the recovered R-APN-amide to produce R-APN. The non-selective hydrolysis step may involve a chemical or an enzymatic reaction. In case of an enzymatic reaction, the enzymes that can be used to catalyze the reaction may include a hydrolase (lipase/acylase/esterase).

In an alternative embodiment, the method for preparing enantiomerically enriched APN begins with the steps of providing a first enantiomeric mixture containing R-APN and S-APN, and non-selectively acylating R-APN and S-APN using a suitable acyl donor to produce a second enantiomeric mixture containing acylated R-APN and acylated S-APN. The second enantiomeric mixture is then used as a substrate in a selective hydrolysis in the presence of a suitable enzyme, as described hereinabove.

The methods for preparing enantiomerically enriched APN may include the steps of reacting the recovered R-APN with methanesulfonic acid to form R-APN-methanesulfonate salt, and recovering the R-APN-methanesulfonate salt.

Other objects and further benefits of the present invention will become apparent to persons having ordinary skill in the art from the following written description and accompanying figures.

DETAILED DESCRIPTION OF THE INVENTION

For the purposes of promoting an understanding of the principles of the invention, specific language will be used to describe exemplary embodiments of the present invention. It will nevertheless be understood that no limitation of the scope of the invention is thereby intended. The invention includes any alterations and further modifications in the illustrated devices and described methods and further applications of the principles of the invention which would normally occur to one skilled in the art to which the invention relates.

The present invention provides methods for producing enantiomerically enriched APN, utilizing stereoselective enzymes for preferential acylation or preferential hydrolysis of one of the enantiomers of APN, followed by the isolation of a specific enantiomer.

The stereoselectivity of acylation or hydrolysis stems from the specific character of location of functional groups within the active center of the enzyme molecule, which favors binding of one stereo-form of the substrate over the other form and provides for higher reactivity of this stereo-form in the acylation or hydrolysis reaction.

Acylation of amino group attached to the stereo-center in the molecule of APN can be achieved in a stereospecific way by reacting an enantiomeric mixture of APN, with an acyl donor in the presence of a selected enzyme, and in specific reaction conditions. A typical enantiomeric mixture of APN is a racemic mixture, having substantially equal amounts of R-APN and S-APN. The acylation reaction may be represented as follows.

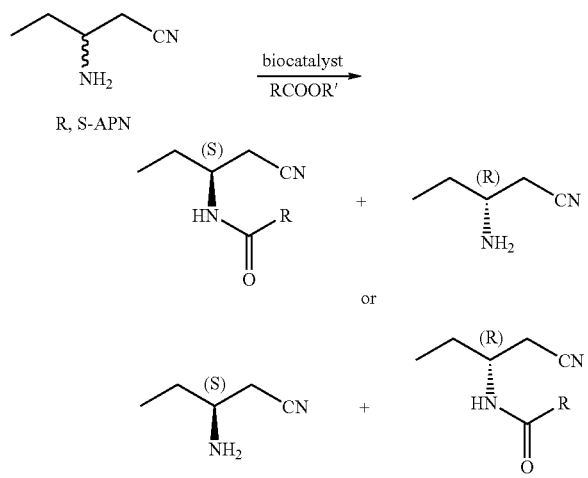

The specific biocatalyst and acyl donor (RCOOR') dictate which reaction pathway will occur, either S-APN will be acylated, leaving R-APN unreacted, or R-APN will be acylated, leaving S-APN unreacted. In either case, a separation of enantiomer can be made. Further, an additional chemical step is required to deacylate the acylated R-APN or acylated S-APN.

For the development of an enzymatic process it is crucial to know whether the enzyme can act on the substrate and the acyl donor. Further, it is equally important to know whether there is any preference for a particular enantiomer. Although compounds capable of being acyl donors are generally known, not all known acyl donors can be used in enzymatic selective acylation.

As descried in EXAMPLE 1 (below), several potential acyl donors have been tested. Many acyl donors spontaneously react with APN and some are not compatible with specific enzymes. The acyl donors that have been shown to acylate APN in the reaction catalyzed by Lipase B include trifluoroethyl butyrate (butyrate TFE); di-trifluoroethyl 1,4-cyclohexane dicarboxylic acid; benzoic acid vinyl ester; butyric acid vinyl ester, caproic acid vinyl ester, lauric acid vinyl ester, butyl vinyl carbonate, 2,6-furan-dimethanol divinyl carbonate, 1,6-hexanediol divinyl carbonate, ethyl acetate, and butyl acetate (See TABLE 1). In addition, the enzymes capable of catalyzing the acylation of APN, other than Lipase B, include Lipase AL, CHIRAZYME L-10, Lipase PL, Lipase QL, CHIRAZYME L-1, Lipase L-10, Lipase AY-30, Lipase Type VII, Lipase "CV", Lipase "PN", Lipase Type 250, Lipase PS-30, Lipase TL, Lipase "RN", Lipase A-10FG, CHIRAZYME L-8, Cholesterol esterase, and CHIRAZYME E-1 (See EXAMPLE 2 and TABLE 2, CHIRAZYME is a registered mark, Roche Corp., Basel, Switzerland).

It has been found that Lipase AL, Lipase PL, Lipase Type VII, Lipase "PN", Lipase TL, CHIRAZYME L-8, CHIRAZYME E-1 are selective towards acylation of S-APN, leaving R-APN non-acylated (See EXAMPLE 3, TABLE 3A).

In contrast, it has been found that CHIRAZYME L-1, CHIRAZYME L-5, Lipase Type 250, and Lipase PS-30 are selective toward acylation of R-APN, leaving S-APN non-acylated (See EXAMPLE 3, TABLE 3B).

As generally is known, the conditions for enzymatic acylation show strong impact on the reaction rate and stereo-selectivity of the catalysts. Below are the results of the studies of the effect of a number of reaction parameters on the enantioselectivity of enzymatic acylation of APN with butyrate TFE with special emphasis paid to the process catalyzed by Lipase TL.

Temperature. The reaction temperature (in the range from 25 to 45° C.) did not show significant impact on stereoselectivity of APN acylation catalyzed by different enzymes in methyl tert butyl ether (MTBE) as a solvent.

Solvent. Application of acetonitrile instead of MTBE afforded smaller enantioselectivity in APN acylation and MTBE was selected as reaction solvent in stereo-resolution of APN. In fact, such solvents as tetrahydrofuran (THF), toluene, pyridine, 1,4-dioxane, and others are known as potential medium for the reaction catalyzed by lipases and esterases.

Reagent concentration. Concentration of butyrate TFE was an important parameter in determining the stereoselectivity of enzymatic acylation in the reaction catalyzed by Lipase TL from *Pseudomonas stutzeri* in MTBE. Increase in the molar excess of the acyl donor over racemic mixture of APN (from 1 to 30 fold) resulted in 1.5–2 fold higher reaction stereospecificity.

Enzyme amount. The reactions of APN acylation with butyrate TFE were performed at constant concentration of the suspension of immobilized enzyme, 10 mg/mL of organic solvents and the effect of the enzyme concentration on the reaction enantioselectivity was not studied. However, as is known from literature, this parameter, as well as the ways of preparing the biocatalyst (enzyme loading on the support, treatment of immobilized enzyme with polar solvents, surfactants, etc.) can influence stereo-selectivity of enzymatic acylation.

Water content. A water content in the solvent from 0.4 to 4 volume % (vol. %) of the solvent is useful (See EXAMPLE 4).

In addition to the acyl donors and the enzymes described above, other acyl donors including methyl phenylacetate, methyl phenoxyacetate, phenylacetamide, and phenylacetic acid may be used with particular enzymes, such as penicillin acylase (See EXAMPLE 5).

Penicillin acylase is also known as penicillin amidase, penicillin G amidase, penicillin amido hydrolase, and penicillin V acylase. The enzyme is available from many com mercial sources, both in immobilized and free forms (See TABLE 2). Penicillin acylase is highly active towards the amide bonds and is active over a broad range of pH (5.4–11.0) and moderate temperature (10–45° C.). Penicillin acylase catalyzed reactions are in general done in aqueous phase, or mainly aqueous medium with the amount of water-miscible organic solvent equal to 10–30 vol. %. The controlled addition of polar organic solvents facilitates the miscibility/solubility of the substrate (APN) keeping penicillin acylase active. The general use of aqueous medium is mainly because of the pre notion that aqueous system is necessary for this enzyme to be active. However, the enzyme has been found to be active in non-aqueous media too. The acylation reaction using penicillin acylase may be performed in a solvent system that may include acetonitrile, methanol, or MTBE (See TABLES 5A–5D), or in a predominantly non-polar organic system that may include MTBE, toluene, ethyl acetate, n-butyl acetate, methylene chloride, and benzene. APN concentration can be in the range of 0.02–0.5 M. A typical concentration of APN is 0.25 M. A concentration range from about 0.04 to 0.5 M of an acyl donor can be used. A typical concentration of an acyl donor is twice of APN concentration. Amount of the enzyme can be in a range of 10–100 mg/mL of reaction mixture.

A model acylation reaction catalyzed by penicillin acylase is demonstrated in EXAMPLE 6. In this reaction, up to about 72% ee$_{R-APN}$ could be achieved after 7 hours of reaction (see TABLE 6).

Penicillin acylase shows enantioselectivity towards acylation of S-APN, leaving R-APN non-acylated, as shown in EXAMPLES 5 and 6. The unreacted R-APN can be separated from acylated S-APN by stripping into an aqueous solution or can be easily collected as a methanesulfonate salt (to be described below). As the relative rates of acylation of R and S enantiomers are considerably different, ee's >99% can be achieved with proper variations of the reaction parameters. The reaction can be performed either in a batch process or in a continuous column reactor.

S-APN-phenylacetamide formed during the course of the enzymatic reaction can be isolated and hydrolyzed by the same enzyme in a water rich environment. The MTBE solution of methyl phenylacetate can be re-circulated.

In another approach, the method for preparing enantiomerically enriched APN involves selective hydrolysis of an enantiomeric mixture containing acylated R-APN and acylated S-APN, in the presence of an enzyme. As demonstrated in the following reaction scheme, penicillin acylase is a suitable enzyme for the selective hydrolysis.

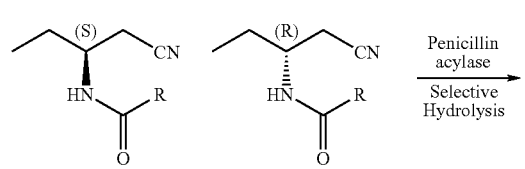

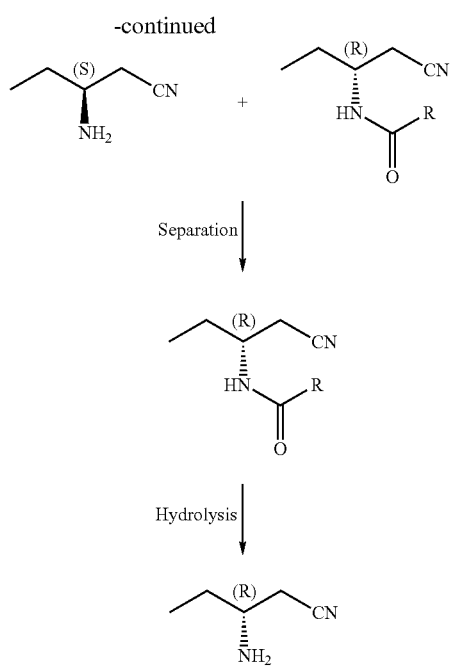

The enantiomeric mixture may contain R-APN-phenylacetamide and S-APN-phenylacetamide. As penicillin acylase is more active towards S-APN, the enzyme catalyzed hydrolysis of the enantiomeric mixture will result in formation of S-APN and R-APN-phenylacetamide (see reaction scheme above). Using any suitable conventional chemical techniques, the products can be separated to S-APN and R-APN-phenylacetamide, which can be further hydrolyzed by the same enzyme or other chemical methods under suitable conditions to produce R-APN.

The selective hydrolysis reactions can be carried out in aqueous, water-water-miscible solvent (5–30 vol. %) such as acetonitrile, methanol, etc., or in a two-phase water-water immiscible non-polar organic solvents over a range of pH's (see EXAMPLE 7).

In an alternative approach, the method for preparing enantiomerically enriched 3-APN begins with acylation of a racemic mixture of APN to produce a racemic mixture of acylated APN. This acylation step is not a selective acylation reaction, therefore both R-APN and S-APN are acylated. The non-selective acylation may involve a chemical reaction (See EXAMPLE 8). Suitable acyl donors for this reaction include phenylacetyl chloride. With phenylacetyl chloride as the donor, the resulting enantiomeric mixture contains substantially equal amounts of S-APN-phenylacetamide and R-APN-phenylacetamide. The resulting enantiomeric mixture of APN-phenylacetamide may be enzymatically selectively hydrolyzed, as described above.

As mentioned earlier, the methods of the present invention may include the step of separating the acylated enantiomer from non-acylated enantiomer of APN. This separating step may be performed using any suitable separation procedure. One example is to react the mixture of acylated S-APN and non-acylated R-APN with dibenzoyl-L tartaric acid, which is selective towards binding to R-APN, to produce R-APN-dibenzoyl-L tartrate salt. The salt may be precipitated and isolated from the mixture, yielding enantiomerically enriched R-APN-dibenzoyl-L tartrate (See EXAMPLE 9). R-APN-dibenzoyl-L tartrate salt may be further reacted with methanesulfonic acid to form R-APN-methanesulfonate salt, which is a useful compound for the production of pharmaceutical molecules.

It is possible that the mixture of acylated enantiomer and non-acylated enantiomer of APN may be reacted directly with methanesulfonic acid, without going through the step of reacting with dibenzoyl-L tartaric acid. In this reaction, R-APN reacts with methanesulfonic acid to form R-APN-methanesulfonate salt (See EXAMPLE 10).

In order to determine the relative amounts of the R- and S-enantiomers of the APN or APN amides, the product of the acylation reaction is analyzed using standard chiral and achiral liquid chromatography techniques. A high performance liquid chromatography (HPLC) may be used to determine the relative proportions of each enantiomer.

An example of analytical protocols for the determination of R— and S-APN is as follows. APN was derivatized initially with o-phthalaldehyde and Boc-L-cysteine and analyzed by HPLC. The derivatization reagent was prepared by adding 128 mg of N-tert-butoxycarbonyl L-cysteine to 50 mg of o-phthalaldehyde, dissolved in 1.0 mL methanol and diluted to 5 mL with a 0.4 N potassium borate buffer of pH 10.4. A 20 µL of the reagent thus prepared was added to 30 µL of APN solution (approximately 2 µmoles), and was diluted further with 40 µL of pH 10.4 borate buffer. The derivatized sample was injected on to a ZORBAX C-18 column (150×4.6 mm) (ZORBAX is a registered trademarks of the Du Pont company, Wilmington, Del.) maintained at 40° C. and eluted isocratically with 75:25 phosphate buffer of pH 6.2 (0.015 M) containing 10% (v/v) acetonitrile. The elution profile was followed at a wavelength of 338 nm using a UV detector.

The result of the HPLC analysis may be used to determine the optical purity in terms of enantiomer excess (% ee), using the following calculation:

% $ee_{R-APN}$=100([R-APN]−[S-APN])/([R-APN]+[S-APN])

% $ee_{S-APN}$=100([S-APN]−[R-APN])/([S-APN]+[R-APN])

A further identification of the enantiomers may be performed using a nuclear magnetic resonance (NMR) technique.

EXAMPLE 1

Acyl Donor Screening

In order to select the acyl donors that do not react spontaneously with APN but could only participate in the reaction catalyzed by enzymes, 67 various acyl donors were tested for the possibility of spontaneous reaction with APN. The acyl donors were selected from the groups of alkyl acetates (OAc), vinyl esters (VE), vinyl carbonates (ViCarb), and trifluoroethyl esters (TFE) of different carboxylic acids. Control reactions of APN (99.5% pure as shown on certificate of analysis as received from DuPont Nylon Specialties) with acyl donors were set up as follows: 0.5 mL APN was dissolved in 20 mL methyl tert-butyl ether (MTBE) (0.25 M). To 0.25 mL of this solution, 20 µL or 20 mg of acyl donors were added and the solutions or suspensions were left at 40° C. overnight. Samples were taken after 14 hours of the reaction time and analyzed by Gas Chromatography (GC). Out of 67 acyl donors, 23 donors showed some spontaneous reaction with APN and were excluded from further studies. The reagents for enzymatic acylation of APN were then selected from the remaining 44 acyl donors.

Selected acyl donors were then tested in the enzymatic acylation of APN catalyzed by *Candida antarctica* lipase B (CHIRAZYME L-2). Lipase B was chosen for screening because this enzyme is known for its high activity and broad substrate specificity in the acylation reactions for different acyl acceptors. The enzyme was added to the reaction mixture in the amount of 10 mg/mL. The GC method used here determined the reaction conversion, but did not allow separate resolution of the acylation products formed by S-APN and R-APN. Thus, the single peak in GC traces corresponded to the enantiomeric mixture of the acylated forms of both S- and R-APN. Thirteen compounds listed in TABLE 1 were tested as acyl donors in the reaction of APN acylation catalyzed by lipase B under the same reaction conditions as those described above.

TABLE 1

Conversion of APN in the reaction with selected acyl donors catalyzed by *Candida antarctica* lipase B, after 18 hours.

| Acyl donor | Conversion (%) |
| --- | --- |
| Butyrate TFE | 100 |
| 1,4-Cyclohexane dicarboxylic acid diTFE | 64 |
| Benzoic acid VE* | 91 |
| Butyric acid VE* | 100 |
| Caproic acid VE* | 100 |
| Lauric acid VE* | 72 |
| Butyl ViCarb* | 18 |
| 2,6-Furan-dimethanol diViCarb* | 100 |
| 1,6-Hexanediol diViCarb* | 12 |
| EtOAc | 68 |
| BuOAc | 91 |

*Several reaction products are formed in the reactions with these acyl donors.

Among different groups of acyl donors, best results were obtained with trifluoroethylacetate (TFE), which showed single products in the reaction with APN (TABLE 1). Butyrate TFE was chosen as the best possible reagent as the reaction with APN resulted in good product yields in a rather short reaction time, which could be practically convenient for developing the process of stereo-resolution of APN. Although the reaction with other TFE compounds proceeds slower, they can also be used as acyl donors for stereo-separation of APN. Other acyl donors in TABLE 1 are less convenient for developing the process of APN stereo-resolution as they may form multiple reaction products. In the reaction with vinyl esters, a small amount of acetaldehyde is formed as a result of the accompanying hydrolysis of vinyl esters and this aldehyde can form the Schiff base in the non-enzymatic reaction with APN as a by-product along with the enzymatically produced amide. Due to bifunctional character of carbonate group, vinyl carbonates can react with two acceptor molecules, which gives rise to several reaction products as well.

EXAMPLE 2

Enzyme (Lipase/Esterase) Screening

Full lipase/esterase screen was set up using butyrate TFE as acyl donor and APN as acceptor of butyrate group. A total of 70 lipase/esterase catalysts was screened. The screen was set up as follows: 2.5 mL of butyrate TFE and 0.9 mL of APN (prepared as previously described) were added to 36 mL of MTBE and the solution was vortexed. Then 0.4 mL of the solution was added to test tubes containing the lipase/protease powders organized in a 9×8 plate and the reactions were shaken at 45° C. GC analysis of the reaction mixtures showed that several enzymes catalyzed the acylation of racemic APN in very high conversions (>80%) (TABLE 2). This fact means that both enantiomers of APN: R-APN and S-APN, were reactive in acylation. These enzymes did not show any pronounced enantioselectivity in the reaction. For this reason, these enzymes were not studied in further experiments. A number of lipases and proteases were not active enough as they showed low conversions (<25%). Therefore, the enzymes showing low conversion were not included in further screening experiments.

Most promising for further catalyst development were the enzymes, which showed conversions for the reaction at around 50±10%. Possible explanation for this number is that in these reactions, only one of the enantiomers (either R-APN or S-APN) reacts with the acyl donor while the other enantiomer remains unreacted. As a result, thirteen enzymes were identified which were further studied as the catalysts for optical resolution of APN (TABLE 2).

Thirteen lipase/esterase catalysts selected from the list in TABLE 2 were further tested in the reaction of APN acylation with butyrate TFE. The reaction conversion was estimated using GC method, and Chiral HPLC allowed the determination of the amount of non-reacted R-APN and S-APN in the reaction mixture. By analyzing the results of these methods used in combination, it is possible to calculate the amounts of both non-reacted and acylated forms for R-APN and S-APN.

TABLE 2

Enzymes used in screening the catalyst for the reaction of APN acylation with TFE butyrate, which showed the reaction conversions at around 50 ± 10%, after 18 hours.

| Enzyme | Source | Support | Producer | Conversion (%) |
|---|---|---|---|---|
| Lipase AL | *Alcaligenes* sp. | Accurel[a] | Meito Sangyo[1] | 54.0 |
| CHIRAZYME L-10 | *Alcaligenes* sp. | Accurel[a] | Roche[2] | 47.1 |
| Lipase PL | *Alcaligenes* sp. | Accurel[a] | Meito Sangyo[1] | 56.5 |
| Lipase QL | *Alcaligenes* sp. | Accurel[a] | Meito Sangyo[1] | 50.1 |
| CHIRAZYME L-1 | *Burkholderia cepacia* | Accurel[a] | Roche[2] | 56.4 |
| Lipase L-10 | *Candida lipolytica* | Accurel[a] | Amano[3] | 47.9 |
| Lipase AY-30 | *Candida rugosa* | Accurel[a] | Amano[3] | 40.9 |
| Lipase Type VII | *Candida rugosa* | Accurel[a] | Sigma[4] | 44.2 |
| Lipase "CV" | *Chromobacterium viscosum* | Accurel[a] | Finn Sugar[5] | 48.6 |
| Lipase "PN" | *Phycomyces nitens* | Accurel[a] | Wako[6] | 49.5 |
| Lipase Type 250 | *Porcine pancreas* | Accurel[a] | Solvay[7] | 55.9 |
| Lipase PS-30 | *Pseudomonas cepacia* | Accurel[a] | Amano[3] | 50.2 |
| Lipase TL | *Pseudomonas stutzeri* | Accurel[a] | Meito Sangyo[1] | 56.0 |
| Lipase "RN" | *Rhizopus niveus* | Accurel[a] | Fluka[8] | 48.9 |
| Lipase A-10FG | *Rhizopus oryzae* | Accurel[a] | Nagase[9] | 58.9 |
| CHIRAZYME L-8 | *Thermomyces sp.* | Accurel[a] | Roche[2] | 50.5 |
| Cholesterol esterase | *Porcine pancreas* | Powder | Sigma[4] | 55.1 |
| CHIRAZYME E-1 | Pig liver | Celite[b] | Roche[2] | 44.4 |

[1]Meito Sangyo Co., Nishi-Ku Nagoya, Japan;

[2]Roche Corp., Basel, Switzerland;

[3]Amano Enzyme Inc., Nagoya, Japan;

[4]Sigma Aldrich Corp., St Luis, MO, USA;

[5]Finnsugar Bioproducts, Helsinki, Finland,

[6]Wako Chemicals GmbH, Neuss, Germany;

[7]Solvay S.A., Brussels, Belgium;

[8]Fluka, Buchs SG, Switzerland;

[9]Nagase, Tokyo, Japan;

[a]Accurel Type EP100 (MP 1004), particle size 200–400 micron, is a product of Akzo Nobel Faser AG, Obernburg, Germany;

[b]Celite Corporation. 2500 Miguelito. Lompoc, CA, USA.

EXAMPLE 3

Enantioselectivity of Selected Enzymes

A primary goal is to find enzymes that can specifically acylate S-APN leaving as much non-reacted R-APN as possible and then separate non-acylated R-APN from S-APN and acylated forms of R- and S-APN. These enzymes should provide for high $ee_{R-APN}$ values. It was found (TABLE 3A) that a number of tested enzymes show this type of enantioselectivity and thus, can be applied for increasing the relative amount of R-APN over S-APN in the acylation reaction mixture. According to their high $ee_{R-APN}$ values, lipases AL and TL are among the best catalysts belonging to this group of enzymes.

TABLE 3A

Enzymes showing high enantioselection towards S-APN in the acylation reaction, yielding high enantiomeric excess of R-APN ($ee_{R-APN}$).

| Lipase/Esterase | Source | Conversion (%) in 24 h | $ee_{R-APN}$ (%) |
| --- | --- | --- | --- |
| AL, *Alcaligenes* sp. | Meito Sangyo | 85 | 70 |
| PL, *Alcaligenes* sp. | Meito Sangyo | 78 | 15 |
| Type VII, *Candida rugosa* | Sigma | 45 | 6 |
| PN, *Phycomyces nitens* | Wako | 68 | 9 |
| TL, *Pseudomonas stutzeri* | Meito Sangyo | 98 | 91 |
| CHIRAZYME L-8, *Thermomyces* sp. | Roche | 86 | 26 |
| CHIRAZYME E-1, pig liver esterase | Roche | 68 | 6 |

A secondary goal is to find enzymes that can specifically acylate R-APN, leaving as much non-acylated S-APN as possible. The acylated R-APN and non-acylated S-APN may then be separated. The separated acylated R-APN may then be hydrolyzed to R-APN by using chemical or enzymatic methods. For successful application here, the enzymes should have high $ee_{S-APN}$ values. Among all tested lipases and esterases, CHIRAZYME L-5 and lipase PS-30 appeared to be the most efficient enzymes from that catalyst group (see TABLE 3B).

TABLE 3B

Enzymes showing high enantioselection towards R-APN in the acylation reaction, yielding high enantiomeric excess of S-APN ($ee_{S-APN}$).

| Lipase/Esterase | Source | Conversion (%) in 24 h | $ee_{S-APN}$ (%) |
| --- | --- | --- | --- |
| CHIRAZYME L-1, *Burkholderia cepacia* | Roche | 99 | 28 |
| CHIRAZYME L-5, *Candida antarctica* | Roche | 99 | 95 |
| Type 250, porcine pancreas | Solvay | 61 | 5 |
| PS-30, *Pseudomonas cepacia* | Amano | 92 | 56 |

EXAMPLE 4

Effect of Water Content on Enzymatic Acylation of Racemic APN

Stereo-selectivity of APN acylation with butyrate TFE catalyzed by different enzymes depended on the content of water in organic solvent, which was determined by using Karl Fisher titration. This conclusion may have significant impact on the practical aspects of stereo-resolution of APN. In order to verify this conclusion, reactions were set up in the presence of different amounts of water added to MTBE. All other conditions include: 1 mL of MTBE, 25 µL racemic APN (prepared as previously described, 75 µL TFE butyrate, 5 mg immobilized lipase, incubated at 45° C. Water saturated solvent was prepared by mixing 2 mL dry MTBE with 2 mL water. The results in TABLE 4 indicates that increasing the water content decreases the enantioselectivity of the enzyme.

TABLE 4

Reaction conversion and product stereo-selectivity achieved in the reaction of APN acylation with butyrate TFE catalyzed by lipase TL *Pseudomonas stutzeri* as a function of different amount of water added to MTBE

| Water content µL/mL MTBE | Conversion (%) 6 hour reaction | $ee_{R-APN}$ (%) 6 hour reaction | Conversion (%) 24 hour reaction | $ee_{R-APN}$ (%) 24 hour reaction |
| --- | --- | --- | --- | --- |
| 4 | 79.5 | 44 | 95.2 | 85 |
| 7 | 74.6 | 38 | 92.6 | 78 |
| 10 | 75.4 | 37 | 93.3 | 78 |
| 15 | 75.0 | 36 | 93.0 | 73 |
| 20 | 74.4 | 32 | 93.2 | 69 |
| 30 | 75.5 | 31 | 93.7 | 66 |
| 40 | 72.5 | 27 | 92.6 | 62 |
| water-saturated | | | 46.3 | 9 |

EXAMPLE 5

Selective Acylation of APN Catalyzed by Penicillin Acylase in Different Buffer Several sets of acylation reactions were prepared using different solvents and reaction conditions. In one set of the reactions, added to each reaction vial were 30 mg/mL of penicillin acylase (PGA-450), 0.1 M phosphate (pH=6.0) or borate (pH=10.4), 0.04 M of racemic mixture of APN, 0.07 M of an acyl donor, and an amount of solvent to make 1.0 mL reaction. The temperature was kept at either 45° C. or at room temperature. The reaction was run for 22 hours, after which the reaction samples were analyzed. The results reported in TABLE 5 indicate that penicillin acylase has a catalytic effect in acylating APN when methyl phenylacetate, or phenylacetamide, was used as the acyl donor. Also indicated is that the enzyme is selective towards acylation of S-APN, leaving R-APN non-acylated.

TABLE 5A

Selective acylation of APN in buffer-polar solvents

| pH | Acyl donor | Temperature (° C.) | solvent | solvent (%) | $ee_{R-AP}$ (%) |
|---|---|---|---|---|---|
| 10.4 | Methyl phenylacetate | 45 | — | — | 6 |
| 10.4 | Methyl phenylacetate | 45 | acetonitrile | 10 | 4 |
| 10.4 | Methyl phenylacetate | 45 | methanol | 10 | 8 |
| 10.4 | Phenylacetamide | 45 | — | — | 0 |
| 10.4 | Phenylacetamide | 45 | acetonitrile | 10 | 2 |
| 10.4 | Phenylacetamide | 45 | methanol | 10 | 4 |
| 6.0 | Methyl phenylacetate | rt | — | — | 2 |
| 6.0 | Phenylacetamide | rt | — | — | 8 |
| 6.0 | Methyl phenylacetate | rt | acetonitrile | 10 | 2 |
| 6.0 | Phenylacetamide | rt | acetonitrile | 10 | 8 |
| 6.0 | Methyl phenylacetate | rt | methanol | 10 | 4 |
| 6.0 | Phenylacetamide | rt | methanol | 10 | 12 |

In another set of reactions, the reaction vials were prepared with phenylacetamide and methyl phenylacetate as the acyl donors in 1.0 mL reaction. PGA-450=30 mg, 0.2 mL buffer (pH=6.0, 0.5 M) were added to each vial, containing 2 μL APN. The reaction samples were analyzed after 24 hours. The results (TABLE 5B) indicate that, at pH 6.0, penicillin acylase is effective in catalyzing acylation of APN. Methanol appears to be a suitable co-solvent. The reaction product shows % $ee_{R-APN}$ of between 1.2 and 26.7.

TABLE 5B

Selective acylation of APN at pH 6.0

| Acyl donor | Acyl donor (M) | solvent (%) | solvent | Temperature (° C.) | $ee_{R-APN}$ (%) |
|---|---|---|---|---|---|
| phenylacetamide | 0.1 | 0 | — | 25 | 6.4 |
| phenylacetamide | 0.1 | 0 | — | 45 | 10.8 |
| phenylacetamide | 0.1 | 10 | Methanol | 25 | 11.8 |
| phenylacetamide | 0.1 | 10 | Methanol | 45 | 12.4 |
| phenylacetamide | 0.1 | 20 | Methanol | 25 | 26.7 |
| phenylacetamide | 0.1 | 20 | Methanol | 45 | 14.3 |
| phenylacetamide | 0.1 | 30 | Methanol | 25 | 12.4 |
| phenylacetamide | 0.1 | 30 | Methanol | 45 | 4.7 |
| phenylacetamide | 0.35 | 0 | — | 25 | 5.2 |
| phenylacetamide | 0.35 | 0 | — | 45 | 19.3 |
| phenylacetamide | 0.35 | 10 | Methanol | 25 | 10.3 |
| phenylacetamide | 0.35 | 10 | Methanol | 45 | 18.1 |
| phenylacetamide | 0.35 | 20 | Methanol | 25 | 21.4 |
| phenylacetamide | 0.35 | 20 | Methanol | 45 | 8.5 |
| phenylacetamide | 0.35 | 30 | Methanol | 25 | 11.0 |
| phenylacetamide | 0.35 | 30 | Methanol | 45 | 1.2 |
| methyl phenylacetate | 0.35 | 80 | MTBE | 25 | 11.2 |
| methyl phenylacetate | 0.35 | 80 | MTBE | 45 | 22.8 |

In another set of reactions, the solvent system was prepared by presaturating MTBE with water. In all reaction vials, 0.6 mL MTBE was added with 20 mg of acyl donor, 10 mg enzyme PGA-450 P and 20 μmoles of APN. Phosphate buffer (pH=6.0; 0.5M) was added to adjust the phase volume ratio. After 18 hours, water was added to each vial to make the total water content equal in all the vials to compensate for evaporation loss. After mixing the aqueous phase was analyzed for % $ee_{R-APN}$ after derivatizing the APN. The data in TABLE 5C indicate that in addition to methyl phenylacetate, methyl phenoxyacetate, and phenylacetic acid could be used as the acyl donors. In the two phase system, penicillin acylase was effective in acylation of APN. The reaction performed at the temperature of 45° C. usually yielded higher % $ee_{R-APN}$, which could reach 33.6%.

TABLE 5C

Selective acylation of APN in a two-phase system

| Acyl donor | Temperature (° C.) | Solvent:aqueous ratio | $ee_{R-APN}$ (%) |
|---|---|---|---|
| Methyl phenylacetate | rt | 0.86 | 17.0 |
| Methyl phenylacetate | rt | 0.80 | 1.4 |
| Methyl phenylacetate | rt | 0.35 | 2.5 |
| Methyl phenylacetate | 45 | 0.86 | 33.6 |
| Methyl phenylacetate | 45 | 0.50 | 3.8 |
| Methyl phenylacetate | 45 | 0.35 | 2.3 |
| Methyl phenoxyacetate | rt | 0.50 | 1.9 |
| Methyl phenoxyacetate | 45 | 0.50 | 2.5 |
| Phenylacetic acid | rt | 0.50 | 0.7 |
| Phenylacetic acid | 45 | 0.50 | 1.7 | rt = room temperature

In another set of experiments, the reaction mixtures were prepared with water saturated MTBE (0.6 mL), with methyl phenylacetate as the acyl donor and 10 mg of PGA-450. A 0.5M phosphate buffer (pH=6.0) was used to adjust the buffer ratio. The enzyme in each vial was pre-equilibrated with the buffer for few minutes, followed by the addition of APN and acyl donor to make a 1.0 mL reaction. The reaction mixture was analyzed at 18 hours and % $ee_{R-APN}$ was determined. The results (TABLE 5D) indicate that in a non-aqueous medium, penicillin acylase catalyzed reactions could result enantiomeric excesses in >99% $ee_{R-APN}$.

TABLE 5D

Selective acylation of APN in predominantly non-aqueous medium: (pH = 6.0)

| Temp. (° C.) | Methyl phenylacetate (M) | Buffer (%) | APN (M) | $ee_{R-APN}$ (%) |
|---|---|---|---|---|
| 40 | 0.2 | 0 | 0.033 | >85 |
| 40 | 0.2 | 0.4 | 0.033 | >99 |
| 40 | 0.2 | 1.7 | 0.033 | >99 |
| 40 | 0.2 | 8.3 | 0.033 | 64.0 |
| 40 | 0.04 | 1.7 | 0.033 | 62.0 |
| 40 | 0.04 | 1.7 | 0.085 | 30.0 |
| 40 | 0.04 | 1.7 | 0.170 | 14.0 |
| 10 | 0.04 | 4.0 | 0.033 | 40.0 |

EXAMPLE 6

Model reaction of Penicillin Acylase Catalyzed Acylation of APN in a Non-Polar Organic Solvent 3.0 g penicillin acylase enzyme (PGA-450), and 0.15 mL water were added to a vial. The vial was then shaken for fifteen minutes and kept at 4° C. overnight for equilibration. To a three-necked 500 mL flask, 100 mL water saturated MTBE, 2.5 mL APN and 7.5 mL methyl phenylacetate were added. The reaction mixture was stirred with an overhead stirrer at room temperature. To this mixture, the equilibrated enzyme was added with continued stirring. The progress of the reaction was followed by analyzing samples taken from the reaction solution using the chiral resolution method described earlier. The enantiomeric excess of R-APN at different time intervals is presented in TABLE 6.

TABLE 6

Increased production of R-APN with increased reaction time

| Time (min.) | $ee_{R-APN}$ (%) |
|---|---|
| 0 | 0.4 |
| 30 | 7.6 |
| 60 | 13.0 |
| 120 | 25.5 |
| 210 | 41.5 |
| 300 | 56.4 |
| 420 | 72.0 |

EXAMPLE 7

Selective Hydrolysis Catalyzed by Penicillin Acylase in Different Buffers

Three sets of reactions were prepared generally as follows. For reactions in buffered media, APN-phenylacetamide was transferred to a 2.5 mL glass vial and to this vial, penicillin acylase (PGA-450) was added followed by the addition of buffer. For reactions in buffer-solvent mixtures, APN-phenylacetamide was dissolved in a solvent/water mixture and a calculated amount of this solution was transferred to the vial following the addition of the enzyme, penicillin acylase (PGA-450) to make up the volume to 1.0 mL, and the contents were stirred continuously with a magnetic stirrer.

The progress of the hydrolysis reaction was followed by determining the concentrations of 3-aminopentanenitrile phenylacetamide and phenylacetic acid formed at different time intervals with an HPLC. The reaction mixture after diluting with acetonitrile was injected on to a PHENOMENEX C18 column (PHENOMENEX is a trademark of Phenomenex, Torrence, Calif.) and eluting with acetonitrile: water mixture (40:60) both containing (0.1% perchloric acid) following the elution profile with a UV detector at 254 nm.

A study (TABLE 7A) indicates that APN-phenylacetamide can be hydrolyzed by penicillin acylase in the presence of a polar solvent, such as acetonitrile. The results show that penicillin acylase is more active towards hydrolysis of S-APN-producing phenylacetamide, producing enantiomeric excess of S-APN, leaving R-APN-phenylacetamide unreacted. In this particular study, 0.1 M APN-phenylacetamide was used. The pH was adjusted with 0.5 M of phosphate or bicarbonate buffer. The analysis was carried out after 18 hours.

TABLE 7A

Hydrolysis of APN-phenylacetamide in the presence of a polar solvent

| PGA-450 (mg) | pH | solvent | $ee_{S-APN}$ (%) |
|---|---|---|---|
| 100 | 6.0 | — | 30 |
| 100 | 7.0 | — | 10 |
| 100 | 8.0 | — | 4 |
| 100 | 9.0 | — | 2 |
| 60 | 6.0 | 5% acetonitrile | 18 |
| 60 | 7.0 | 5% acetonitrile | 8 |
| 60 | 8.0 | 5% acetonitrile | 10 |
| 60 | 9.0 | 5% acetonitrile | 10 |

The study (TABLE 7B) indicates that the selective hydrolysis of APN-may phenylacetamide may also be performed using a solvent including MTBE. The pH of the reaction may also varied from about 6 to about 9. In this particular experiment, 65 μmoles APN-phenylacetamide was used with 10 mg of the enzyme, PGA-450. The reactions were buffered with 0.025 mL of 0.5 M solution of phosphate and bicarbonate. For % ee determination, the solvent of the reaction mixture was dried under a stream of nitrogen, water was added to make up the volume to 1.0 mL, and analyzed by HPLC.

TABLE 7B

Hydrolysis of APN-phenylacetamide by PGA-450 in the presence of MTBE

| pH | Temperature (° C.) | Total volume (mL) | Solvent-aqueous ratio | $ee_{S-APN}$ (%) |
|---|---|---|---|---|
| 6.0 | 25 | 0.6 | 0.83 | 24.0 |
| 6.0 | 25 | 1.0 | 0.50 | 31.2 |
| 6.0 | 45 | 0.6 | 0.83 | 21.7 |
| 6.0 | 45 | 1.0 | 0.50 | 22.2 |
| 7.0 | 25 | 0.6 | 0.83 | 24.0 |
| 7.0 | 25 | 1.0 | 0.50 | 26.3 |
| 7.0 | 45 | 0.6 | 0.83 | 24.4 |
| 7.0 | 45 | 1.0 | 0.50 | 18.9 |
| 8.0 | 25 | 0.6 | 0.83 | 16.4 |
| 8.0 | 25 | 1.0 | 0.50 | 21.1 |
| 8.0 | 45 | 0.6 | 0.83 | 20.1 |
| 9.0 | 25 | 0.6 | 0.83 | 28.3 |
| 9.0 | 25 | 1.0 | 0.50 | 28.1 |

TABLE 7B-continued

Hydrolysis of APN-phenylacetamide by PGA-450 in the presence of MTBE

| pH | Temperature (° C.) | Total volume (mL) | Solvent-aqueous ratio | $ee_{S\text{-}APN}$ (%) |
|---|---|---|---|---|
| A | 25 | 0.6 | 0.83 | 21.3 |
| A | 25 | 1.0 | 0.50 | 19.7 |

A - represents unbuffered solution

The study in TABLE 7C indicates that selective hydrolysis of APN-phenylacetamide may be performed in a two-phase solvent system at relatively low pH (4.7–6.0). In this study, the reactions were buffered by phosphate (pH=6.0), acetate (pH=4.7), citrate (pH=5.5) and formate (pH=5.5$^x$). 10 mg PGA-450, 0.02 mL buffer solution (0.5 M), and 65 µmoles of APN-phenylacetamide were present in each vial. A two phase solvent system containing 1:1 ratio of MTBE to aqueous phase was used. The product from aqueous phase was analyzed (% $ee_{S\text{-}APN}$ was determined).

TABLE 7C

Selective hydrolysis of APN-phenylacetamide in two phase system

| pH | Temperature (° C.) | $ee_{S\text{-}APN}$ (%) |
|---|---|---|
| 6.0 | 40 | 25.2 |
| 6.0 | Rt | 28.8 |
| 6.0 | 10 | 33.4 |
| 4.7 | 40 | 25.0 |
| 4.7 | Rt | 31.5 |
| 4.7 | 10 | 34.5 |
| 5.5 | 40 | 22.7 |
| 5.5 | Rt | 29.7 |
| 5.5 | 10 | 34.6 |
| 5.5$^x$ | 40 | 18.8 |
| 5.5$^x$ | Rt | 27.2 |
| 5.5$^x$ | 10 | 33.5 |

EXAMPLE 8

Production of 3-APN-Phenylacetamide by a Chemical Reaction

The acylation (amidation) reaction was carried out under Schotten-Baumann conditions, as follows. Dissolve 5 g of NaOH in 50 mL water and add 5 mL of a racemic mixture of APN (4.665 g; d=0.933; 0.0475 moles; M.W.=98.15) and add 8 mL phenylacetyl chloride (9.3 g; 0.06 moles) and stir for 2 hrs at room temperature. Extract the amide with ethyl acetate (30 mL) and wash the ethyl acetate layer with water. Remove the solvent by rotary evaporation with acetone/dry-ice trap. The compound was further dried after adding few mL of methanol and removing the solvent. The precipitate formed was collected and dried in a desiccator under vacuum. Yield=8.7 grams (85%) and the product was confirmed by NMR.

EXAMPLE 9

Production of R-Aminopentanenitrile Dibenzoyl-L-Tartaric Acid Salt

Racemic APN (5 mL) and butyrate TFE (15 mL) were added to 0.2 L of MTBE. Then 1.0 g of lipase TL (*Pseudomonas stutzeri*) produced by Meito Sangyo and immobilized on Accurel was added and the suspension was incubated at 45° C. in a thermostated shaker (250 rpm) for 8 hours. The reaction was stopped by cooling the suspension down to 20° C. and filtering off the immobilized catalyst on a glass funnel with paper filter. After concentrating the reaction mixture to an oil, the oil was diluted with ethyl acetate. Next 0.7 meq of dibenzoyl-L-tartaric acid in ethyl acetate/water (8:1) was added and the solids collected. Chiral HPLC analysis of the solid revealed a 26% S-APN and 74% R-APN (ee. 48%).

EXAMPLE 10

Production of R-Aminopentanenitrile Methanesulfonic Acid Salt

Racemic APN (0.25M), methyl phenylacetate (0.5M) and 3 g of penicillin acylase (penicillin G amidase) in 100 mL of water saturated MTBE were mixed at room temperature. At various times, samples were removed and analyzed by HPLC. The reaction was terminated by filtering off the enzyme after 7 hours when the ee of the product (R-APN) was >72%. The enzyme was washed with additional MTBE, which was then added to the reaction solution.

A sample of 110 mL of reaction solution was concentrated under reduced pressure to give an oil. This oil was diluted with 7 mL EtOAc and 1.1 mL methanesulfonic acid (MsOH) was added and stirred at room temperature for 16 hours. The slurry was cooled to 0–5° C. and the solids collected by filtration. The cake was washed with EtOAc (2×25 mL) and dried (45° C., house vacuum) to give a white solid containing R-APN-methanesulfonic acid salt (R-APN-MsOH) (0.67 g, 87% ee, 59% yield).

While the invention has been illustrated and described in detail in the foregoing description, the same is to be considered as illustrative and not restrictive in character. It should be understood that only the exemplary embodiments have been shown and described and that all changes and modifications that come within the spirit of the invention are desired to be protected.

What is claimed is:

1. A method for preparing enantiomerically enriched 3-aminopentanenitriles comprising the steps of:
   providing an enantiomeric mixture containing R-3-aminopentanenitrile R-APN) and S-3-aminopentanenitrile (S-APN): and
   reacting the enantiomeric mixture with an acyl donor in the presence of an enzyme to selectively acylate one of R-APN and S-APN;
   wherein the enzyme includes penicillin acylase.

2. The method of claim 1, wherein the acyl donor is selected from the group comprising phenylacetic acid, methyl phenylacetate, methyl phenoxyacetate, and phenylacetamide.

3. The method of claim 2, wherein the reacting step is performed in the presence of an organic solvent.

4. The method of claim 3, wherein the organic solvent is methyl tert butyl ether.

* * * * *